US005155199A

United States Patent [19]

Hayashi

[11] Patent Number: 5,155,199

[45] Date of Patent: Oct. 13, 1992

[54] MAKEUP MATERIAL FOR HUMAN USE

[75] Inventor: Shunichi Hayashi, Nagoya, Japan

[73] Assignee: Mitsubishi Jukogyo Kabushiki Kaisha, Tokyo, Japan

[21] Appl. No.: 426,989

[22] Filed: Oct. 25, 1989

[30] Foreign Application Priority Data

Oct. 31, 1988 [JP] Japan ........................ 63-273345

[51] Int. Cl.[5] ........................ C08G 18/10; C08G 18/32

[52] U.S. Cl. ........................ 528/65; 528/44; 528/59; 528/66; 528/83; 528/84; 528/85; 521/99; 521/159; 521/163; 424/78.03; 514/72; 514/953

[58] Field of Search ........................ 528/44, 65, 59, 66, 528/83, 84, 85; 524/524; 521/99, 159, 163; 514/72, 953; 424/78

[56] References Cited

U.S. PATENT DOCUMENTS

| | | | |
|---|---|---|---|
| 4,945,127 | 7/1990 | Kagawa et al. | 524/524 |
| 5,037,178 | 8/1991 | Stoy et al. | 428/34.9 |
| 5,049,591 | 9/1991 | Hayashi et al. | 521/159 |

OTHER PUBLICATIONS

"Development of Polymeric Elasticity Memory Material", Mitsubishi Juko GIHO vol. 25, No. 3 (1988) pp. 236–240.

*Primary Examiner*—John Kight, III
*Assistant Examiner*—Duc Truong
*Attorney, Agent, or Firm*—McAulay Fisher Nissen Goldberg & Kiel

[57] ABSTRACT

Disclosed is a makeup material for human use containing a shape memory polymer shaped into fine spheres. The shape memory polymer used is a polyurethane that is obtained by polymerizing with the prepolymer method a composition of a bifunctional diisocyanate, a bifunctional polyol, and a bifunctional chain extender with active hydrogen groups in the mole ratio of diisocyanate:polyol:chain extender=2.00–1.10:1.00:1.00–0.10. The polyurethane is preferred to have approximately equal amounts of NCO groups and OH groups at its ends, and a glass transition point above the human body temperature, and a crystallinity value between 3 to 50 wt %.

1 Claim, No Drawings

MAKEUP MATERIAL FOR HUMAN USE

FIELD OF THE INVENTION AND RELATED ART STATEMENT

The present invention relates to a makeup material for human use and, in particular, to a makeup material for concealing wrinkles and unevenness on human skin.

Makeup materials and cosmetics used on human skin usually comprise such materials as various kinds of perfume, petrolatum (vaseline), animal fat, vegetable oil, and pigments, and are used as foundation, rogue, or various types of cream.

Recently, synthetic resins with shape memory have attracted much attention. A number of specific uses and technology for such shape memory synthetic resins have been developed in various fields (see, for example, Japanese Patent Applications Nos. 145774/1984, 191/1985, 47585/1985, 72572/1985, 134338/1985, 134339/1985, and 159441/1988).

Large changes in the elasticity of these synthetic resins around the glass transition point can be utilized as follows. A synthetic resin is first heated to temperatures higher than its glass transition point so that it becomes soft, and then it is formed into desired shapes. While being held in these shapes, the resin is cooled to temperatures below its glass transition point so that its shapes are fixed as they are. The fixed shapes can be erased easily to restore the original shapes by heating the resin above the glass transition point.

In a quite different context, now that it is fashionable to keep and make one's appearance look younger, surgical operations for removing wrinkles on a face and use of cosmetics such as the ones mentioned above to cover up wrinkles with thick coating are popular among not only women but also men.

However, the former is expensive, and impossible for those who cannot be operated on for their weak constitution or some other reasons.

Also, the latter is troubled by the cracking or partial peeling off of the makeup after a long period of time or during vigorous workout, or by too much time consumed when applying the cosmetics.

Therefore, if wrinkles can be concealed by the thin application of a makeup material, the above problems will resolve altogether.

The present inventors, after intensive research on this problem, have come up with the idea of mixing a synthetic resin having shape memory noted above into cosmetics and utilizing the glass transition point of the synthetic resins which is above the human body temperature.

However, the synthetic resins having shape memory as proposed above can become highly difficult to form into free shapes because, for example, urethane elastomers have many excess NCO groups which cause bridging reactions at the ends of their molecular chains, forming net-like high polymer compounds.

Thus, because these resins are difficult to form into spherical shapes small enough to be used as an ingredient for a makeup material, it would be difficult or impossible, the inventors predict, to produce an inexpensive makeup material for making wrinkles disappear using the above urethane elastomers with shape memory.

OBJECT AND SUMMARY OF THE INVENTION

It is an object of the present invention to provide a makeup material using a shape memory polymer which can be easily shaped into particles having more or less spherical shapes and which has a glass transition point above the human body temperature and, more specifically, provide a makeup material for removing wrinkles at low cost.

The present invention relates to a makeup material containing fine, round particles of a shape memory polymer. As a polymer used in the present invention, preferred is a polyurethane that is obtained by polymerizing with the prepolymer method a composition of a bifunctional diisocyanate, a bifunctional polyol, and a bifunctional chain extender with active hydrogen groups in the mole ratio of diisocyanate:polyol:chain extender=2.00–1.10:1.00:1.00–0.10. This polyurethane is preferred to have approximately equal amounts of NCO groups and OH groups at its ends, and its glass transition point should be above the human body temperature, and its crystallinity is preferred to be between 3 to 50 wt %.

The prepolymer method for synthesizing a urethane elastomer will be explained below.

First, a diisocyanate and a polyol are let react with each other at a specific value of the mole mixing ratio of A =[NCO]/[OH], to synthesize a prepolymer. After this reaction is completed, a chain extender is added so that a desired value for the mole ratio of B=[chain extender]/[prepolymer] is achieved. The bridging reaction is carried out at 80° C. for 1 to 2 days to synthesize a urethane elastomer. The above synthesis may be carried out in solvent or without solvent.

The glass transition point (Tg) and physical properties can be influenced by such factors as: (1) the kind of isocyanate; (2) the kind of polyol; (3) the kind of chain extender; (4) the mixing ratio A; (5) the mixing ratio B; and (6) annealing. By changing the factors (1) to (6), we can synthesize a urethane elastomer with a desired value for Tg and physical properties.

We can produce the makeup material of the present invention by mixing small, more or less round particles of a shape memory polymer into ordinary ingredients for cosmetics such as perfume, petrolatum (vaseline), animal fat, vegetable oil, and pigments.

This makeup material is heated to temperatures above the glass transition point (Tg) of the shape memory polymer formed into fine, spherical or round particles as described above and is applied thinly to facial skin with large shearing force. The above-mentioned polymer, being soft and expanded, then covers small wrinkles (grooves) and unevenness of the facial skin with the action of the strong shearing force. It then cools down to the facial temperature and hardens and contracts.

The polymer, having hardened and contracted, conceals the wrinkles and unevenness by pulling the two side faces of the grooves (wrinkles) or higher portions around lower areas together to close depressions. In this situation, because the makeup material of the present invention is spread very thinly, it will not crack or peel off even after a long period of time or during vigorous physical activities. Also, the application of the makeup material is easy because it can be done simply by heating up the material slightly and spreading it thinly. Furthermore, in order to remove the makeup material from the face, heat is used to bring its temperature above Tg so that the polymer will return to the original, nearly round shape. The makeup material can then be removed with small force.

DETAILED DESCRIPTION OF PREFERRED EMBODIMENTS

The shape memory polymers that can be used for the makeup material of the present invention are polymers related to, for example, urethane, styrene and/or butadiene, crystalline diene, and norbornane.

Among these, polyurethane is preferred. In the present invention, preferred is a polyurethane that is obtained by polymerizing with the prepolymer method a composition of a bifunctional diisocyanate, a bifunctional polyol, and a bifunctional chain extender with active hydrogen groups in the mole ratio of diisocyanate:chain extender =2.00-1.10:1.00-1.00-0.10. This polyurethane is preferred to have approximately equal amounts of NCO groups and OH groups at its ends, and its glass transition point should be above the human body temperature, and its crystallinity is preferred to be between 3 to 50 wt %.

Because this polyurethane does not have excess NCO groups at the ends of a molecule, the bridging reaction does not occur and it remains a chain molecule. Furthermore, because of the values noted above for the crystallinity, the polyurethane shows thermoplasticity and can be shaped into small, more or less spherical particles easily and well.

As a bifunctional diisocyanate for an ingredient of the above polyurethane, one that can be used is described by the following general formula: OCN—R—NCO, where R means one or two phenylene groups or without R at all. To be more specific, 2,4-toluene diisocyanate, 4,4'-diphenylmethane diisocyanate, 4,4'-diphenylmethane diisocyanate modified with carbodiimide, or hexamethylene diisocyanate, for example, can be used.

Also, as a bifunctional polyol, one that can be used is described by the following general formula: OH—R'—OH, where R' means one or two phenylene groups or without R' at all. It can also be, for example, a reaction product of a bifunctional polyol and a bifunctional carboxylic acid or a cyclic ether. To be more specific, polypropylene glycol, 1,4-butaneglycol adipate, polytetramethylene glycol, polyethylene glycol, a reaction product of bisphenol (bisphenol-A) and a propylene oxide, for example, can be used.

As a bifunctional chain extender containing active hydrogen groups, one that is described by the following general formula can be used: OH—R"—OH, where R" means a $(CH_2)_n$ group, or one or two phenylene groups. It can also be, for example, a reaction product of the chain extender and a bifunctional carboxylic acid or a cyclic ether. To be more specific, ethylene glycol, 1,4-butane glycol, bis(2-hydroxylethyl)hydroquinone, a reaction product of bisphenol (bisphenol-A) and ethylene oxide, or a reaction product of bisphenol (bisphenol-A) and propylene oxide, for example, can be used.

The polyurethane in the present invention manufactured from the above-mentioned ingredients is expressed by the following general formula:

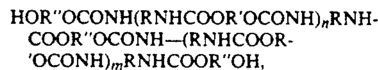

HOR"OCONH(RNHCOOR'OCONH)$_n$RNHCOOR"OCONH—(RNHCOOR'OCONH)$_m$RNHCOOR"OH, where m=1-16, n=0-16, and R, R', and R" are as noted above.

In order to shape this polymer into small, more or less spherical particles, such a method as the one described below is preferred. First, the polymer is formed into pellets and cooled down to very low temperatures using, for example, liquid nitrogen. Then, the polymer is broken into fine powder by applying mechanical force, and this fine powder is heated until it melts, and then it is solidified.

As an alternative to this mechanical method, a chemical method can be used. In the chemical method the polymer is dissolved into a solvent such as DFM (dimethylformamide) or the mixture of DFM and MEK (methylethylketone). Then, this solvent containing the polymer is mixed and stirred into another solvent whose boiling point is higher than the former and which does not dissolve the polymer. The resulting suspension is heated to evaporate the solvent. Fine, round particles of the polymer result.

The polymer particles is preferred to be approximately 5-10 μm in diameter.

EMBODIMENTS 1 to 40

[1] Preparation of Shape Memory Polymers Shaped Into Fine, More or Less Spherical Particles The preparation of the polymers in the present invention can be done, for example, by the following procedure.

Polyurethanes were prepared using the compositions shown in Table 1 and then kept at less than −150° C. with liquid nitrogen. With the application of external force, the polyurethanes were finely powdered and then heated to more than 180° C. until they melted and solidified to have the shape memory polymers shaped into fine particles of more or less spherical shape.

In Table 1, E/E' equals to (tensile elastic modulus at Tg−10° C.)/(tensile elastic modulus at Tg+10° C.), and the crystallinity was measured by the X-ray diffraction method.

TABLE 1

| Raw materials and molar ratio | M.W. | 1 | 2 | 3 | 4 | 5 | 6 | 7 | 8 | 9 | 10 |
|---|---|---|---|---|---|---|---|---|---|---|---|
| Diisocyanate | | | | | | | | | | | |
| 2,4-toluene diisocyanate | 174 | 1.5 | | | 1.5 | | | | | | |
| 4,4'-diphenylmethane diisocyanate | 250 | | | | | 1.5 | | | 1.5 | 1.5 | 1.5 |
| 4,4'-diphenylmethane diisocyanate (carbodiimide-modified) | 290 | | | | | | 1.5 | | | | |
| 4,4'-diphenylmethane diisocyanate (carbodiimide-modified) | 303 | | 1.5 | 1.5 | | | | | | | |
| hexamethylene diisocyanate | 168 | | | | | | | 1.5 | | | |
| Polyol | | | | | | | | | | | |

TABLE 1-continued

| | | | | | | | | | | | |
|---|---|---|---|---|---|---|---|---|---|---|---|
| polypropylene glycol | 400 | | | | | | | | | | |
| polypropylene glycol | 700 | | | 1.0 | 1.0 | 1.0 | 1.0 | 1.0 | 1.0 | 1.0 | 1.0 |
| polypropylene glycol | 1000 | | 0.88 | | | | | | | | |
| 1,4-butaneglycol adipate | 600 | | | | | | | | | | |
| 1,4-butaneglycol adipate | 1000 | | | | | | | | | | |
| 1,4-butaneglycol adipate | 2000 | | | | | | | | | | |
| polytetramethylene glycol | 650 | | | | | | | | | | |
| polytetramethylene glycol | 850 | | | | | | | | | | |
| polytetramethylene glycol | 1000 | | | | | | | | | | |
| polyethylene glycol | 600 | | | | | | | | | | |
| bisphenol-A + propylene oxide | 800 | 1.0 | | | | | | | | | |
| Chain extender | | | | | | | | | | | |
| ethylene glycol | 62 | | | | | | | | 0.51 | | |
| 1,4-butane glycol | 90 | 0.51 | | | | | | | | 0.51 | |
| bis(2-hydroxyethyl) hydroquinone | 198 | | | | | | | | | | |
| bisphenol-A + ethylene oxide | 327 | | | | | | | | | | |
| bisphenol-A + ethylene oxide | 360 | | 0.51 | 0.51 | 0.51 | 0.51 | 0.51 | 0.51 | | | |
| bisphenol-A + propylene oxide | 360 | | | | | | | | | | 0.51 |
| Measured values of physical properties | | | | | | | | | | | |
| Tg (°C.) | | 24 | −10 | 15 | −11 | 14 | 16 | −45 | 9 | 6 | 12 |
| E/E' | | 170 | 73 | 69 | 23 | 129 | 133 | 20 | 117 | 128 | 97 |
| Crystallinity (wt %) | | | 20 | 20 | 30 | | | 25 | | | |
| | | 11 | 12 | 13 | 14 | 15 | 16 | 17 | 18 | 19 | 20 |
| Diisocyanate | | | | | | | | | | | |
| 2,4-toluene diisocyanate | 174 | | | | | | | | | | |
| 4,4'-diphenylmethane diisocyanate | 250 | 1.5 | 1.5 | 1.5 | 1.2 | 1.8 | 1.35 | 1.35 | 1.35 | 1.35 | 1.35 |
| 4,4'-diphenylmethane diisocyanate (carbodiimide-modified) | 290 | | | | | | | | | | |
| 4,4'-diphenylmethane diisocyanate (carbodiimide-modified) | 303 | | | | | | | | | | |
| hexamethylene diisocyanate | 168 | | | | | | | | | | |
| Polyol | | | | | | | | | | | |
| polypropylene glycol | 400 | | | | | | | | | | |
| polypropylene glycol | 700 | 1.0 | 1.0 | | 1.0 | 1.0 | 1.0 | | | | |
| polypropylene glycol | 1000 | | | | | | | 1.0 | | | |
| 1,4-butaneglycol adipate | 600 | | | | | | | | 1.0 | | |
| 1,4-butaneglycol adipate | 1000 | | | | | | | | | 1.0 | |
| 1,4-butaneglycol adipate | 2000 | | | | | | | | | | 1.0 |
| polytetramethylene glycol | 650 | | | | | | | | | | |
| polytetramethylene glycol | 850 | | | | | | | | | | |
| polytetramethylene glycol | 1000 | | | | | | | | | | |
| polyethylene glycol | 600 | | | 1.0 | | | | | | | |
| bisphenol-A + propylene oxide | 800 | | | | | | | | | | |
| Chain extender | | | | | | | | | | | |
| ethylene glycol | 62 | | | | | | | | | | |
| 1,4-butane glycol | 90 | | | | | | | | | | |
| bis(2-hydroxyethyl) hydroquinone | 198 | | 0.51 | | | | | | | | |
| bisphenol-A + ethylene oxide | 327 | 0.51 | | | 0.21 | 0.81 | 0.36 | 0.36 | 0.36 | 0.36 | 0.36 |
| bisphenol-A + ethylene oxide | 360 | | | | | | | | | | |
| bisphenol-A + propylene oxide | 360 | | | | | | | | | | |
| Measured values of physical properties | | | | | | | | | | | |
| Tg (°C.) | | 16 | −7 | −6 | −4 | 25 | 5 | −22 | 10 | −18 | −45 |
| E/E' | | 111 | 49 | 12 | 105 | 53 | 37 | 81 | 100 | 29 | 30 |
| Crystallinity (wt %) | | | 20 | 30 | | 20 | 25 | | | 25 | 25 |
| | | 21 | 22 | 23 | 24 | 25 | 26 | 27 | 28 | 29 | 30 |
| Diisocyanate | | | | | | | | | | | |
| 2,4-toluene diisocyanate | 174 | | | | | | | 1.5 | 1.4 | 1.3 | 1.2 |

TABLE 1-continued

| | | | | | | | | | | | |
|---|---|---|---|---|---|---|---|---|---|---|---|
| 4,4'-diphenylmethane diisocyanate | 250 | 1.35 | 1.35 | 1.35 | 1.5 | 1.5 | 1.35 | | | | |
| 4,4'-diphenylmethane diisocyanate (carbodiimide-modified) | 290 | | | | | | | | | | |
| 4,4'-diphenylmethane diisocyanate (carbodiimide-modified) | 303 | | | | | | | | | | |
| hexamethylene diisocyanate | 168 | | | | | | | | | | |
| Polyol | | | | | | | | | | | |
| polypropylene glycol | 400 | | | | | | 1.0 | | | | |
| polypropylene glycol | 700 | | | | 1.0 | 1.0 | | | | | |
| polypropylene glycol | 1000 | | | | | | | | | | |
| 1,4-butaneglycol adipate | 600 | | | | | | | | | | |
| 1,4-butaneglycol adipate | 1000 | | | | | | | | | | |
| 1,4-butaneglycol adipate | 2000 | | | | | | | | | | |
| polytetramethylene glycol | 650 | 1.0 | | | | | | | | | |
| polytetramethylene glycol | 850 | | 1.0 | | | | | | | | |
| polytetramethylene glycol | 1000 | | | 1.0 | | | | | | | |
| polyethylene glycol | 600 | | | | | | | | | | |
| bisphenol-A + propylene oxide | 800 | | | | | | | 1.0 | 1.0 | 1.0 | 1.0 |
| Chain extender | | | | | | | | | | | |
| ethylene glycol | 62 | | | | | | | | | | |
| 1,4-butane glycol | 90 | | | | | | | | | | |
| bis(2-hydroxyethyl) hydroquinone | 198 | | | | | | | 0.51 | 0.41 | 0.31 | 0.21 |
| bisphenol-A + ethylene oxide | 327 | 0.36 | 0.36 | 0.36 | 0.43 | 0.35 | 0.36 | | | | |
| bisphenol-A + ethylene oxide | 360 | | | | | | | | | | |
| bisphenol-A + propylene oxide | 360 | | | | | | | | | | |
| Measured values of physical properties | | | | | | | | | | | |
| Tg (°C.) | | −18 | −30 | −38 | 5 | 8 | 23 | 26 | 21 | 19 | 19 |
| E/E' | | 33 | 18 | 40 | 33 | 100 | 126 | 140 | 125 | 108 | 101 |
| Crystallinity (wt %) | | 25 | 25 | | 25 | 15 | 15 | 10 | 15 | 15 | 15 |
| | | 31 | 32 | 33 | 34 | 35 | 36 | 37 | 38 | 39 | 40 |
| Diisocyanate | | | | | | | | | | | |
| 2,4-toluene diisocyanate | 174 | | | 1.5 | | | | | | | |
| 4,4'-diphenylmethane diisocyanate | 250 | 1.59 | 1.68 | | 1.3 | 1.7 | 1.59 | 1.68 | 1.5 | 1.5 | 1.81 |
| 4,4'-diphenylmethane diisocyanate (carbodiimide-modified) | 290 | | | | | | | | | | |
| 4,4'-diphenylmethane diisocyanate (carbodiimide-modified) | 303 | | | | | | | | | | |
| hexamethylene diisocyanate | 168 | | | | | | | | | | |
| Polyol | | | | | | | | | | | |
| polypropylene glycol | 400 | | | | | | | | | | |
| polypropylene glycol | 700 | 1.0 | 1.0 | | 1.0 | 1.0 | 1.0 | 1.0 | | | |
| polypropylene glycol | 1000 | | | | | | | | | | |
| 1,4-butaneglycol adipate | 600 | | | | | | | | | | |
| 1,4-butaneglycol adipate | 1000 | | | | | | | | | | |
| 1,4-butaneglycol adipate | 2000 | | | | | | | | | | |
| polytetramethylene glycol | 650 | | | | | | | | | | |
| polytetramethylene glycol | 850 | | | | | | | | | | |
| polytetramethylene glycol | 1000 | | | | | | | | | | |
| polyethylene glycol | 600 | | | | | | | | | | |
| bisphenol-A + propylene oxide | 800 | | | 1.0 | | | | | 1.0 | 1.0 | 1.0 |
| Chain extender | | | | | | | | | | | |
| ethylene glycol | 62 | | | | 0.31 | 0.71 | 0.51 | 0.51 | | | |
| 1,4-butane glycol | 90 | | | | | | | | 0.51 | | |
| bis(2-hydroxyethyl) hydroquinone | 198 | | | 0.51 | | | | | | 0.51 | 0.81 |
| bisphenol-A + ethylene oxide | 327 | | | | | | | | | | |
| bisphenol-A + ethylene oxide | 360 | 0.51 | 0.51 | | | | | | | | |

TABLE 1-continued

| | | | | | | | | | | |
|---|---|---|---|---|---|---|---|---|---|---|
| bisphenol-A + propylene oxide | 360 | | | | | | | | | |
| Measured values of physical properties | | | | | | | | | | |
| Tg (°C.) | 10 | 11 | 22 | 2 | 15 | 11 | 12 | 35 | 40 | 48 |
| E/E' | 126 | 126 | 107 | 83 | 122 | 100 | 135 | 124 | 138 | 152 |
| Crystallinity (wt %) | 15 | 20 | 15 | 20 | 15 | 15 | 10 | 10 | 5 | 5 |

The preparation and use of the makeup material will be described by way of a tested example below.

[2] Preparation of the Makeup Material

The fine spheres of shape memory polyurethane of No. 39 composition in Table 1 were mixed by 10 wt % together with 0.5 wt % of rose essence as a perfume, 50 wt % of petrolatum (vaseline), 39.5 wt % of camellia oil as a vegetable oil to prepare the makeup material of the present invention.

[3] Usage of the Makeup Material

The makeup material prepared as above was heated to 45° C., which is above Tg, and applied thinly over one's face with strong shearing force using human hands. After application, the makeup material was let cool and solidify, and the wrinkles and unevenness observed on the face were concealed completely.

Then, the face with the makeup material was washed with water to find no peeling off of the makeup material. The wrinkles and unevenness remained concealed after washing. Also, after 12 hours from the application of the makeup material, no cracking or peeling off of the makeup material was observed.

The makeup material could be washed away easily using warm water at around 42°-43° C.

As we have described above, the makeup material of the present invention shows the following advantages:

(1) According to the present invention, wrinkles and unevenness on the human face can be concealed easily without resorting to surgical operations and without using thick layers of conventional cosmetics.

(2) Thus, using the makeup material of the present invention, those who cannot be operated on may easily conceal wrinkles and unevenness on their skin.

(3) Because the very thin application of the makeup material of the present invention can cover up the wrinkles and unevenness, putting on makeup does not consume too much time. Even long after the application or during vigorous physical activities, the makeup material does not crack or partially peel off.

(4) The shape memory polyurethanes of the present invention do not have excess NCO groups at the ends of their molecular chains, and the bridging reaction associated with excess NCO groups therefore does not occur. Thus, the polymer compounds remain linear and can be formed into free shapes.

This makes the polyurethanes very easy to form into small, nearly spherical shapes suitable for the use as a makeup material. An inexpensive makeup material for concealing wrinkles can thus be prepared.

Considering the advantage that no operation is necessary and only thin application is required, the makeup material of the present invention does not require much cost to conceal wrinkles and unevenness without much costs.

What is claimed is:

1. A make-up material comprising a shape memory polymer shaped into fine particles of more or less spherical shape wherein said polymer is a polyurethane that is obtained by polymerizing with a prepolymer method a composition of a bifunctional diisocyanate, a bifunctional polyol, and a bifunctional chain extender with active hydrogen groups in the mole ratio of diisocyanate:polyol:chain extender=2.00-1.10:1.00:1.00-0.10, said polyurethane having approximately equal amounts of NCO groups and OH groups at its ends, said polyurethane having a glass transition point above human body temperatures, and said polyurethane having a crystallinity value which is between 3 to 50 wt. %.

* * * * *